United States Patent [19]

Inoi

[11] Patent Number: 5,010,109

[45] Date of Patent: Apr. 23, 1991

[54] ANTIMICROBIAL AGENT COMPOSITION

[75] Inventor: Takeshi Inoi, Yokohamashi, Japan

[73] Assignee: Chisso Corporation, Japan

[21] Appl. No.: 347,227

[22] Filed: May 4, 1989

[30] Foreign Application Priority Data

Jun. 30, 1988 [JP] Japan .................................. 63-162983

[51] Int. Cl.$^5$ ............................................. A01N 31/00
[52] U.S. Cl. ................................................... 514/714
[58] Field of Search ........................ 514/714; 568/569

[56] References Cited

U.S. PATENT DOCUMENTS 4,036,890 7/1977 Ester et al. ........................... 568/569

FOREIGN PATENT DOCUMENTS 61-196961 9/1986 Japan .

OTHER PUBLICATIONS

Chemical Abstracts (104: 11168h) (1986).
Chemical Abstracts (107:120872k) (1987).

Primary Examiner—Stanley J. Friedman
Assistant Examiner—Kevin Weddington
Attorney, Agent, or Firm—Leydig, Voit & Mayer

[57] ABSTRACT

A novel antimicrobial, aromatic and deodorizing agent composition and a method of reducing microbial concentration or inhibiting microbial growth using the composition are provided, which composition comprises a zeolote or porous glass carrier and a saturated monoterpene hydroperoxide as an active ingredient, the monoterpene hydroperoxide preferably selected from pinane hydroperoxide, thujane hydroperoxide, carane hydroperoxide, bornane hydroperoxide, paramenthane hydroperoxide, metamenthane hydroperoxide, and mixtures of the foregoing, etc.

20 Claims, No Drawings

ANTIMICROBIAL AGENT COMPOSITION

BACKGROUND OF THE INVENTION

1. Field of the Invention

This invention relates to an antimicrobial agent composition. More particularly, it relates to an antimicrobial agent composition comprising a saturated monoterpene hydroperoxide as an active ingredient.

The above-mentioned substance of the present invention has mild and yet sufficient antimicrobial properties in the living sphere of human being including space. Thus, the composition of the present invention is particularly preferred to be used as a multipurpose antimicrobial agent composition in hospitals, various shops, domestic rooms, cars, etc.

2. Description of the Related Art

Heretofore, physical-chemical processes for sterilizing the living area of human being under constantly mild conditions, have been employed. The physical process includes a process using an ultraviolet lamp, but it has been inconvenient in that it does not pervade the whole area and can damage the eyes. As a chemical process, the scattering of dialdehydes such as glutaraldehyde and the like, have been known, but since such compounds are hydrated, the vapor pressure of the resulting substances is so low that their effect may not reach the whole space to be treated. With recent improvements in hygiene, a multifunctional antimicrobial, aromatic and deodorizing agent having aromatic and deodorizing properties, in addition to an antimicrobial function has been in demand.

The present inventor has made extensive research into the development of an antimicrobial agent having none of the drawbacks described above and providing also aromatic and deodorizing effects. As a result it has been found that the monoterpene hydroperoxide derivatives previously discovered by the present inventors to exhibit aromatic and deodorizing effects (Japanese patent application laid-open No. Sho 61-196,961/1986) surprisingly also function as basically superior and mild antimicrobial agents.

SUMMARY OF THE INVENTION

As apparent from the foregoing, the object of the present invention is to provide a novel antimicrobial, aromatic and deodorizing agent comprising a saturated monoterpene hydroperoxide as an active ingredient, and also a composition containing the agent.

The present invention provides composition (1) as the main embodiment and compositions (2) to (6) as preferred embodiments:

(1) An antimicrobial agent composition comprising a saturated monoterpene hydroperoxide as an active ingredient.

(2) An antimicrobial agent composition according to item (1) wherein said saturated monoterpene hydroperoxide is at least one bicyclic monoterpene hydroperoxide selected from the group consisting of pinane hydroperoxide, thujane hydroperoxide, carane hydroperoxide and bornane hydroperoxide.

(3) An antimicrobial agent composition according to item (1) wherein said saturated monoterpene hydroperoxide is at least one monocyclic monoterpene hydroperoxide selected from the group consisting of paramenthane hydroperoxide and metamenthane hydroperoxide.

(4) An antimicrobial agent composition according to item (1) wherein said saturated monoterpene hydroperoxide is a mixture of at least one bicyclic monoterpene hydroperoxide with at least one monocyclic monoterpene hydroperoxide.

(5) An antimicrobial agent composition according to item (1) wherein said saturated monoterpene hydroperoxide is blended with at least one member selected from the group consisting of water, organic solvents, perfumes, surfactants, inorganic carriers, organic carriers, auxiliaries, and spraying agents.

(6) A composition according to item (5) wherein said inorganic carriers are zeolite or porous glass.

(7) A composition according to item (5) wherein said organic carriers are liquid paraffin, waxes, oils and fats, soaps, cyclodextrin and polyols as auxiliaries.

DETAILED DESCRIPTION OF PREFERRED EMBODIMENTS

Concrete examples of the monoterpene hydroperoxide used in the present invention are bicyclic compounds such as pinane hydroperoxide, thujane hydroperoxide, carane hydroperoxide, bornane hydroperoxide, etc. monocyclic compounds such as paramenthane hydroperoxide, metamenthane hydroperoxide, etc. and optional mixtures of the foregoing.

Any of these hydroperoxides are obtained according to a process disclosed in Japanese patent application laid-open No. Sho 61-196,961/1986 which describes a process for the preparation of the hydroperoxides, in which generally, air or oxygen is directly passed through pinane, thujane, carane, bornane, paramenthane, metamenthane, mixtures of the foregoing or solutions of the foregoing in the presence of a metal such as Ni, Fe, Cu, etc. The reaction rate may be followed according to iodometry. It is unnecessary to complete the reaction, but it is practical in the aspect of energy conservation, to hold the conversion to the peroxides at about 60% or lower, preferably 10 to 50%. If necessary, it is possible to separate the hydroperoxides with a high purity, but even a mixture thereof with the starting material may be fully satisfactory for use as antimicrobial agents. The saturated terpenes are also useful as diluents and stabilizers for the hydroperoxides.

The antimicrobial properties of pinane hydroperoxide, thujane hydroperoxide and paramenthane hydroperoxide as the hydroperoxides upon wet rubbish and organic sludge were observed. The results are shown in the following Table 1.

TABLE 1

| | Antimicrobial tests of pinane hydroperoxide (qualitative) | | | |
|---|---|---|---|---|
| | Wet rubbish (used tea leaves) | | Organic sludge | |
| Elapsed days | Pinane hydroperoxide (0.5%) | Control | Pinane hydroperoxide (0.5%) | Control |
| 0 d | Fragrant; unchanged appearance | Used tea leaves | Fragrant; pale yellow | Sludge smell; brown |
| 10 d | Fragrant; | Putrid smell; | Fragrant; | Putrid smell; |

TABLE 1-continued

Antimicrobial tests of pinane hydroperoxide (qualitative)

| Elapsed days | Wet rubbish (used tea leaves) | | Organic sludge | |
|---|---|---|---|---|
| | Pinane hydroperoxide (0.5%) | Control | Pinane hydroperoxide (0.5%) | Control |
| | unchanged appearance | black-brown | yellow | black-brown |
| 20 d | Fragrant; brown | Strong putrid smell; original form collapsed | Fragrant; yellow | Strong putrid smell; green algae appeared |
| 30 d | Fragrant; brown | Strong putrid smell; no original form | Fragrant; yellow-brown | Strong putrid smell; green and black algae appeared |

(Note)
Used tea leaves were used as wet rubbish and a sludge at the flow-in part of facilities for treating waste water from a chemical factory was used as organic sludge. The water contents therein were both adjusted to 100%. Pinane hydroperoxide was made up into a 0.5% dispersion with a nonionic surfactant.

With other hydroperoxides, similar effects were confirmed.

Next, with pinane hydroperoxide, the respective minimum growth concentrations of various microorganisms were measured. An inoculating microbial liquor was subjected to smear culture on a plate medium having pinane hydroperoxide added in varying amounts and thereafter the minimum concentration inhibiting the growth was measured. A mixed liquor of 55% by weight of pinane hydroperoxide with 45% by weight of pinane was used. The results are shown in Table 2.

TABLE 2

Measurement results of the minimum growth-inhibiting concentration (Concentration unit: ppm)

| Tested fungi | Measurement results |
|---|---|
| Bacillus subtilis ATCC 6633 | 156 |
| Escherichia coli IFO 3301 | 625 |
| Pseudomonas aeruginosa IIDP-I | 5,000 |
| Staphylococcus aureus IFO 13276 | 313 |
| Streptococcus faecalis IFO 12964 | 1,250 |
| Aspergillus niger IFO 4407 | 313 |
| Pecicillium citrium IFO 7784 | 313 |
| Cladosporium cladosporioides IFO 6348 | 156 |
| Hansenula anomala var. anomala IFO 10213 | 156 |

After the minimum growth-inhibiting concentration was measured, organic substances in the system were examined according to high-speed liquid chromatography. As a result, pinane hydroperoxide was almost absent and the presence of 2-pinanol in its place was confirmed. In the present invention, it is not intended to discuss the mechanism of the antimicrobial function of the hydroperoxides, but it is presumed that the hydroperoxides release active oxygen when contacted with microbial bodies of microorganisms to be oxidized and thereby exhibit an antimicrobial function. In the process the hydroperoxides themselves are converted into fragrant alcohols corresponding thereto.

As to substances to be blended in the composition, any substances may be used in principle unless they are substances which damage the antimicrobial properties of the hydroperoxides or those which damage the stability of the hydroperoxides.

The present invention will be described in more detail by way of Examples. Percentages and parts described in the examples are by weight.

EXAMPLE 1

Ethanol was added to a mixture of pinane hydroperoxide (53%) with pinane (47%) (hereinafter referred to as 53:47 stock solution) to prepare a 1% solution, followed by placing 64.3 g of the solution and commercially available Freon gas F-12 (85%)-commercially available LPG (15%) in a 180 ml capacity vessel equipped with a spraying valve under cooling. There was obtained a composition having physical properties of slight combustibility and an initial spraying pressure of about 4.5 Kg/cm$^2$.

This composition was sprayed into a closed vessel having a volume of about 4 m$^3$. The sprayed quantity was about 0.65 g in terms of the 53:47 stock solution. The numbers of the floating bacteria at the respective times in the vessel were measured 24 hours and 48 hours after the spraying. To measure the numbers of floating bacteria, a Petri dish of 90 mm in diameter containing an agar medium (20 ml) as a plate was exposed inside the vessel for 30 minutes, followed by closing the Petri dish and culturing at 370° C. for 48 hours to measure the number of colonies formed.

The numbers of colonies in a control and prior to the spraying were both 16. The numbers of colonies 24 hours and 48 hours after the spraying were 8 and 0, respectively. Thus, a superior space-purifying effect was exhibited.

EXAMPLE 2

Ethanol was added to a mixture (one part) of thujane with thujane hydroperoxide in a ratio of 90:10, obtained by oxidizing thujane and the 53:47 stock solution mentioned in Example 1 (one part) to prepare a 1.5% solution. This solution was made up into a composition in the same manner as in Example 1.

The numbers of floating bacteria inside the vessel were measured in the same manner as in Example 1. The numbers of colonies in a control and prior to the spraying were 17 and 15, respectively, but those 24 hours, 48 hours and 72 hours after the spraying were 10, 2 and 0, respectively.

EXAMPLE 3

Water was added to powdery agar (1.2 part), xanthane gum (0.2 part), glycerin (3.0 parts) and green note perfume (small quantity), to make the whole 100 parts, followed by dissolving it together on heating, cooling down to about 50° C., adding POE (60) sorbitol tetraoleate (0.3 part) to make the whole uniform and cooling to obtain a gel-form antimicrobial agent composition.

EXAMPLE 4

Water was added to carboxymethyl cellulose (3 parts), a nonionic surfactant (2 parts) and 53:47 stock solution (4 parts) to make the whole 100 parts, followed by adding a trivalent metal curing agent (0.3 part), vigorously agitating the mixture to make it uniform and allowing it to stand to obtain a gel-form antimicrobial agent composition.

EXAMPLE 5

A pine perfume (a small quantity) was added to 53:47 stock solution (20 parts), hexylene glycol (5 parts) and sodium stearate (4 parts), followed by heating the mixture to 80° C. and allowing to cool down to obtain a stable gel-form antimicrobial agent composition.

EXAMPLE 6

Water was added to 96% ethyl alcohol (40 parts), 3-methyl-3-methoxybutanol (30 parts), a citron or lemon perfume (5 parts) and 53:47 stock solution (5 parts) to make the whole 100 parts, followed by uniformly agitating to obtain an antimicrobial agent composition in the form of solution, and impregnating it with a suitable quantity of zeolite or porous glass to obtain the respective granular antimicrobial agent composition.

EXAMPLE 7

A fat-oil mixture of beef tallow (70 parts) with coconut oil (30 parts) was saponified with sodium hydroxide to prepare a soap material, followed by adding 53:47 stock solution (2.5 parts) and sodium hyaluronate having a molecular weight of about 800,000 (2 parts), adding, if necessary, a perfume, kneading the mixture, casting it into a frame, cooling and solidifying an antimicrobial soap.

In the above Examples, too, the number of floating bacteria in the vessel was measured in the same manner as in Example 1 and similar effects to those of Examples 1 and 2 were exhibited.

What we claim:

1. An antimicrobial agent composition comprising a zeolite carrier and a saturated monoterpene hydroperoxide as an active ingredient.

2. An antimicrobial agent composition according to claim 1 wherein said saturated monoterpene hydroperoxide is at least one bicyclic monoterpene hydroperoxide selected from the group consisting of pinane hydroperoxide, thujane hydroperoxide, carane hydroperoxide and bornane hydroperoxide.

3. An antimicrobial agent composition according to claim 1 wherein said saturated monoterpene hydroperoxide is at least one monocyclic monoterpene hydroperoxide selected from the group consisting of paramenthane hydroperoxide and metamenthane hydroperoxide.

4. An antimicrobial agent composition according to claim 1 wherein said saturated monoterpene hydroperoxide is a mixture of at least one bicyclic monoterpene hydroperoxide with at least one monocyclic monoterpene hydroperoxide.

5. An antimicrobial agent composition according to claim 1 wherein said saturated monoterpene hydroperoxide is blended with at least one of water, organic solvents, perfumes, surfactants, auxiliaries, and spraying agents.

6. A method of reducing microbial concentration or inhibiting microbial growth comprising treating an area with an antimicrobial composition which includes a zeolite carrier and a saturated monoterpene hydroperoxide as an active ingredient.

7. A method according to claim 6 wherein said saturated monoterpene hydroperoxide is at least one bicyclic monoterpene hydroperoxide selected from the group consisting of pinane hydroperoxide, thujane hydroperoxide, carane hydroperoxide and bornane hydroperoxide.

8. A method according to claim 6 wherein said saturated monoterpene hydroperoxide is at least one monocyclic monoterpene hydroperoxide selected from the group consisting of paramenthane hydroperoxide and metamenthane hydroperoxide.

9. A method according to claim 6 wherein said saturated monoterpene hydroperoxide is a mixture of at least one bicyclic monoterpene hydroperoxide with at least one monocyclic monoterpene hydroperoxide.

10. A method according to claim 6 wherein said saturated monoterpene hydroperoxide is blended with at least one of water, organic solvents, perfumes, surfactants, auxiliaries, and spraying agents.

11. An antimicrobial agent composition comprising a porous glass carrier and a saturated monoterpene hydroperoxide as an active ingredient.

12. An antimicrobial agent composition according to claim 11 wherein said saturated monoterpene hydroperoxide is at least one bicyclic monoterpene hydroperoxide selected from the group consisting of pinane hydroperoxide, thujane hydroperoxide, carane hydroperoxide and bornane hydroperoxide.

13. An antimicrobial agent composition according to claim 11 wherein said saturated monoterpene hydroperoxide is at least one monocyclic monoterpene hydroperoxide selected from the group consisting of paramenthane hydroperoxide and metamenthane hydroperoxide.

14. An antimicrobial agent composition according to claim 11 wherein said saturated monoterpene hydroperoxide is a mixture of at least one bicyclic monoterpene hydroperoxide with at least one monocyclic monoterpene hydroperoxide.

15. An antimicrobial agent composition according to claim 11 wherein said saturated monoterpene hydroperoxide is blended with at least one of water, organic solvents, perfumes, surfactants, inorganic carriers, organic carriers, auxiliaries, and spraying agents.

16. A method of reducing microbial concentration or inhibiting microbial growth comprising treating an area with an antimicrobial composition which includes a porous glass carrier and a saturated monoterpene hydroperoxide as an active ingredient.

17. A method according to claim 16 wherein said saturated monoterpene hydroperoxide is at least one bicyclic monoterpene hydroperoxide selected from the group consisting of pinane hydroperoxide, thujane hydroperoxide, carane hydroperoxide and bornane hydroperoxide.

18. A method according to claim 16 wherein said saturated monoterpene hydroperoxide is at least one monocyclic monoterpene hydroperoxide selected from the group consisting of paramenthane hydroperoxide and metamenthane hydroperoxide.

19. A method according to claim 16 wherein said saturated monoterpene hydroperoxide is a mixture of at least one bicyclic monoterpene hydroperoxide with at least one monocyclic monoterpene hydroperoxide.

20. A method according to claim 16 wherein said saturated monoterpene hydroperoxide is blended with at least one of water, organic solvents, perfumes, surfactants, auxiliaries, and spraying agents.

* * * * *